(12) United States Patent
Pagani et al.

(10) Patent No.: US 6,552,224 B2
(45) Date of Patent: Apr. 22, 2003

(54) PROCESS AND PLANT FOR THE PRODUCTION OF UREA

(75) Inventors: Giorgio Pagani, Lugano (CH); Federico Zardi, Breganzona (CH); Domenico Romiti, Lugano (CH)

(73) Assignee: Urea Casale S.A., Lugano-Besso (CH)

( * ) Notice: Subject to any disclaimer, the term of this patent is extended or adjusted under 35 U.S.C. 154(b) by 0 days.

(21) Appl. No.: 10/049,687

(22) PCT Filed: Feb. 2, 2001

(86) PCT No.: PCT/EP01/01098

§ 371 (c)(1),
(2), (4) Date: May 16, 2002

(87) PCT Pub. No.: WO01/96287

PCT Pub. Date: Dec. 20, 2001

(65) Prior Publication Data

US 2002/0151749 A1 Oct. 17, 2002

(30) Foreign Application Priority Data

Jun. 15, 2000 (EP) .............................. 00112688

(51) Int. Cl.$^7$ .............................................. C07C 273/04
(52) U.S. Cl. .................. 564/70; 66/67; 66/71; 66/72
(58) Field of Search .............................. 564/66, 67, 70, 564/71, 72

(56) References Cited

FOREIGN PATENT DOCUMENTS

WO    WO 96/23767 A1    8/1996

*Primary Examiner*—Peter O'Sullivan
(74) *Attorney, Agent, or Firm*—Sughrue Mion, PLLC

(57) ABSTRACT

A process for urea production in a synthesis loop based on $CO_2$ stripping is distinguished by the fact that at least part of a flow recycle carbamate is sent to a treatment of carbamate decomposition and removal of free ammonia to obtain a vapour flow containing $CO_2$ and $NH_3$ with minimum content of water, and a weak water carbamate solution sent back to a urea recovery unit URS and being at least part of above vapour flow containing $CO_2$ and $NH_3$ with minimum content of water directly fed to the bottom zone of a reaction space.

10 Claims, 2 Drawing Sheets

PROCESS AND PLANT FOR THE PRODUCTION OF UREA

Figure 3:
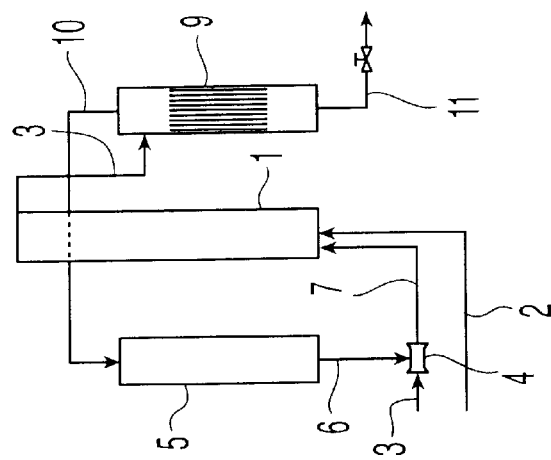

This application is a 371 of PCT/EP01/01098 filed Feb. 2, 2001.

DESCRIPTION

1. Technical Field

In its general aspect the present invention relates to an urea production high efficiency, low investment synthesis loop based on a $CO_2$ stripping scheme with horizontal lay-out.

2. Prior Art

Most of the today new urea plants are based on the so called "stripping" technologies, namely $CO_2$ stripping by Stamicarbon and Toyo and ammonia "self stripping" by Snamprogetti.

All above technologies are characterised by a practically isobaric loop where the main part of unreacted residual $CO_2$ and ammonia contained in the urea reactor effluent are removed in a first carbamate decomposer (stripper), which vapours effluents are at least partially condensed, generating steam in a carbamate condenser. Reactor, stripper and carbamate condenser being the main components of the isobaric loop.

In all above schemes the urea solution effluent from the "stripper" is processed in a downstream urea recovery unit to totally remove the residual content of ammonia and $CO_2$ from urea water solution, forming a water carbamate solution which is recycled to the loop. According to the Snamprogetti and Toyo schemes, a separate stream of liquid ammonia, besides the carbamate solution, is also recycled to the loop.

All above schemes operate with high content of water in the reactor, since most of the water contained in the carbamate water solution recycled from the downstream the loop urea recovery unit is fed to the reaction space (reactor). Such high water content ($H_2O/CO_2$ mole ratio at reactor inlet: 0.5–0.8) prevent to obtain high intrinsic $CO_2$ conversion yields which are essential to minimise the size of equipment and therefore investments and energy consumption for low operating costs. High intrinsic $CO_2$ conversion yields can be obtained only with low water content such as 0.1–0.2 $H_2O/CO2$ mole ratio at reactor inlet.

In addition, in all above schemes (except the Snamprogetti one and improved Toyo $CO_2$ stripping processes) most of the inert gas introduced in the loop—such as for instance air, hydrogen, etc. the main part of which is contained in the $CO_2$ feed (air is generally added for its oxygen content which is used to passivate and protect against corrosion the loop equipment)—reaches the reactor with negative effect on $CO_2$ conversion efficiency.

Key features of the just mentioned technologies are

A) The $CO_2$ stripping processes (namely Stamicarbon and Toyo): ($a_1$) gravity circulation of vapours and liquid streams in the loop, leading to a "vertical lay-out" to secure the above by gravity circulation; ($a_2$) all $CO_2$ feed is sent to the stripper and then to the reactor through the carbamate condenser where vapours are only partially condensed in order to secure the reactor thermal balance; ($a_3$) high water content (high $H_2O/CO_2$ ratio) in the reactor since most of the water contained in the carbamate solution recycle coming from loop downstream urea recovery unit, is sent to the reactor through the loop carbamate condenser.

Modifications in the $CO_2$ stripping processes have been recently introduced by Stamicarbon (AIChE Ammonia Safety Symposium, Boston September 1996) and by Toyo (U.S. Pat. No. 5,936,122), both aiming to achieve horizontal lay-outs to reduce investments and for easier maintenance and operation.

Above modified schemes can be summarized as follow:

Modified Stamicarbon $CO_2$ stripping process (FIG. 1 according to AIChE Boston 1996 publication):—use of an horizontal "pool reactor" where the functions of carbamate condensation with steam generation and reaction to form urea are combined in one single horizontal equipment, being the circulation of liquid and vapour streams from "pool reactor" to stripper still by gravity. The horizontal "pool reactor" is located at a higher level above the top of the stripper to secure the gravity circulation of the loop streams.

Figure 2:
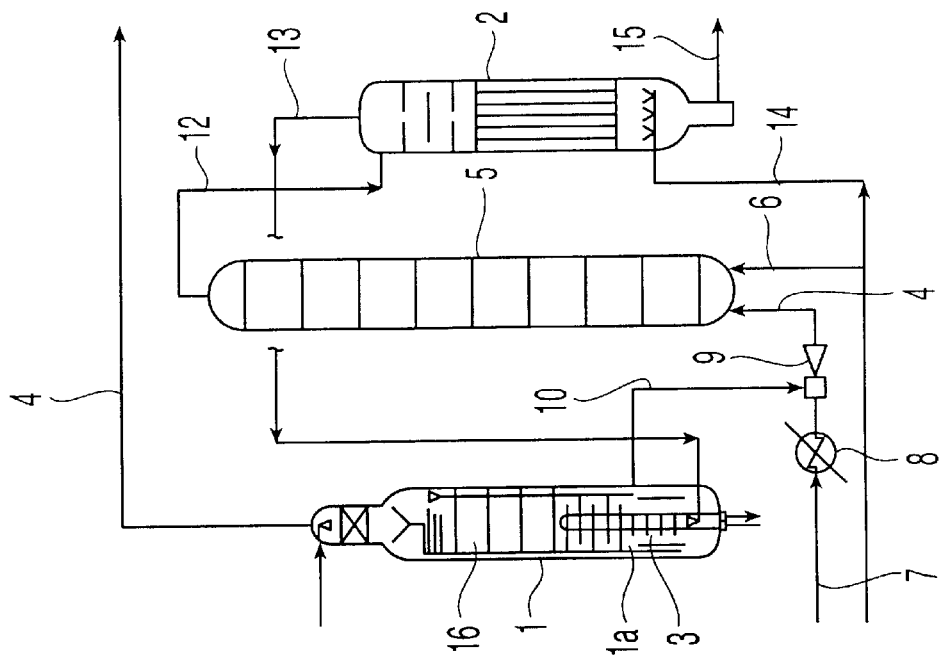

Modified Toyo $CO_2$ stripping process (FIG. 2 according to U.S. Pat. No. 5,936,122): use of a vertical "pool condenser" where the vapours coming from $CO_2$ stripper are totally condensed with steam generation and beginning of urea formation. The carbamate solution from carbamate condenser is recycled to the reactor by the use of an ejector with liquid ammonia as driving fluid. Only part of the $CO_2$ feed is sent to the stripper since part of it has to be sent to the reactor to secure the reactor thermal balance.

B) The Snamprogetti process (FIG. 3 according to UK patent 1188051): ($b_1$) no external stripping agent is used in the stripper, being reactants, including $CO_2$, sent directly to the reactor; ($b_2$) vapours from the stripper are totally condensed in the loop carbamate condenser; ($b_3$) carbamate solution from carbamate condenser recycled to the reactor by the use of an ejector with liquid ammonia used as driving fluid; ($b_4$) high free ammonia residual content in the urea solution effluent from stripper; ($b_5$) high water content (high $H_2O/CO_2$ mole ratio) in the reactor since most of the water contained in the carbamate solution recycle coming from loop downstream urea recovery unit, is sent to the reactor through the loop carbamate condenser; ($b_6$) "horizontal lay-out" where all loop main equipment (reactor stripper and carbamate condenser) are located at ground level.

The following draw-backs are present in the above described loop schemes:

The improved Stamicarbon $CO_2$ stripping process still has a high water content (high $H_2O/CO_2$ mole ratio) in the reactor since most of the water contained in the carbamate solution recycle coming from the loop downstream urea recovery unit is sent to the reacting zone through the carbamate condensation zone of the "pool reactor". That means that the reactor cannot have an intrinsic high efficiency. In addition, the horizontal pool reactor has to be installed at high elevation with high investment costs. High investment costs are also required due to the complexity of the "pool condenser".

In the above schemes high content of inerts are present in the reactor, causing lower $CO_2$ conversion efficiency.

The modified Toyo $CO_2$ stripping process realises the horizontal lay-out but, similarly to the Snamprogetti self stripping process but does not solve the problem of achieving a reaction intrinsic high efficiency with a low $H_2O/CO_2$ mole ratio. In addition, the partial use of the $CO_2$ feed to the stripper (a substantial part of the $CO_2$ feed has to be sent to the reactor) significantly reduces the stripping efficiency with higher residual content of unreacted ammonia and $CO_2$ being left in the stripper urea solution effluent to be processed with high investment and operating costs in the loop downstream urea recovery unit. In addition, high investment costs are required due to the complexity of the "pool condenser".

The Snamprogetti process: although it realises an horizontal lay-out, it does not solve the problem of obtaining intrinsic high efficiency with low ammonia $H_2O/CO_2$ mole ratio like in the other above mentioned processes. In addition, the Snamprogetti self stripping process, with no use of an external stripping agent, causes a higher residual content of free ammonia in the stripper urea solution effluent with higher investment and operating costs in the downstream urea recovery unit.

SUMMARY OF THE INVENTION

The aim of the present invention is to conceive and make available a process and plant related to an urea production high efficiency, low investment synthesis loop based on a $CO_2$ stripping scheme with horizontal lay-outwhich comprises the steps of:

- performing a reaction between ammonia ($NH_3$) and carbon dioxide ($CO_2$) in a vertical reaction space (reactor R) to obtain a mixture comprising urea with minimum residual content of unreacted $CO_2$ (maximum $CO_2$ intrinsic conversion yield) in presence of minimum content of water ($H_2O$) and possibly of High Efficiency Trays (HET);
- subjecting said reaction mixture to a stripping treatment with the use of $CO_2$ feed as stripping agent in a counter current apparatus (Stripper) to remove most of the unreacted $CO_2$ and $NH_3$ and to obtain a first flow comprising $NH_3$ and $CO_2$ in vapour phase and a second flow comprising urea and residual carbamate and free $NH_3$ in aqueous solution, such residual carbamate and free $NH_3$ being removed downstream the loop in a urea recovery unit, and recycled to the loop in a third flow aqueous solution (carbamate recycle solution: CRS) according to means (urea recovery unit: URU) to separate the urea product in aqueous solution;
- subjecting said first flow comprising $NH_3$ and $CO_2$ in vapour phase to total condensation in a carbamate condenser to obtain a carbamate solution which is sent to the reactor space preferably the bottom zone thereof) using an ejector E;
- removing the heat formed in $NH_3$ and $CO_2$ total condensation in the carbamate condenser by producing steam preferably also used to preheat the $NH_3$ feed sent to the reactor and the carbamate solution recycle sent to carbamate stripper;
- in a preferred embodiment above carbamate condenser is designed to be a vertical heat exchanger and to work "full of liquid";
- separation and removal from carbamate condenser top head of main part of inerts (mainly air introduced through the $CO_2$ to protect equipment against corrosion) contained in the vapours effluent from the stripper;
- subjecting at least part of said third flow (carbamate recycle solution CRS) to a treatment (carbamate stripper) for carbamate decomposition and removal of free ammonia to obtain a vapour flow containing $CO_2$ and $NH_3$ with minimum content of water, and a weak water carbamate solution sent back to the urea recovery unit URU;
- in a preferred embodiment above carbamate stripper is designed to be a counter current vertical heat exchanger with trays in the upper head;
- in a preferred embodiment above carbamate recycle solution CRS is preheated, before being sent to the carbamate stripper, with steam, preferably with the steam generated in the carbamate condenser;
- feeding the above vapour flow containing $CO_2$ and $NH_3$ with minimum content of water directly to the loop and preferably to the bottom zone of the reactor space;
- feeding at least part of the $NH_3$ feed through ejector to said reaction bottom space together with carbamate solution stream from carbamate condenser;
- in a preferred embodiment the above $NH_3$ feed is preheated with steam, preferably with the steam generated in the above condenser before being sent to the reactor;
- feeding reactor effluent from upper part of top reaction space to stripping treatment with the use of most, preferably total amount of $CO_2$ feed.

Advantageously, according to the invention, all above-mentioned loop components operate practically isobarically with the following features:

- the vapour flow coming flow the carbamate stripper (preferably of counter current vertical type with trays in upper head), containing $CO_2$ and $NH_3$ with minimum content of water, fed directly to the reactor, secure the heat balance of the same without the need to use substantial part of the $CO_2$ feed to be sent to the reactor to sustain the reactor heat balance;
- most $CO_2$ feed (more than 90%) can be used in the stripper for an efficient $CO_2$ stripping of urea solution effluent from reactor;
- maximum $CO_2$ intrinsic conversion yield in presence of minimum content of water ($H_2O$) and High Efficiency Trays in the reactor;
- maximum efficiency of the stripper even if not all $CO_2$ feed is sent to the stripper as a consequence of the high intrinsic conversion yield and minimum content of water. Stripping efficiencies as good or better than the one of the most efficient conventional $CO_2$ stripper can be obtained even if not all the $CO_2$ feed is sent to the stripper;
- the total condensation in the carbamate condenser (preferably of "full of liquid" vertical shape) of the vapours comprising $NH_3$ and $CO_2$ coming from the $CO_2$ stripper, to obtain a carbamate solution, significantly increase the carbamate solution residence time in the condenser with formation of urea which contribute to increase the total reaction zone residence time;
- the total condensation in the Carbamate Condenser is obtained removing heat as steam which is conveniently used among other users also to preheat the $NH_3$ feed sent to reactor, and the carbamate solution recycle sent to Carbamate Stripper, to secure minimum energy consumption;
- the total condensation of $NH_3$ and $CO_2$ vapours in the carbamate condenser allows the recycle of carbamate solution with the use of ejector driven by at least part of $NH_3$ feed, with all loop main components: carbamate condenser, stripper, reactor and carbamate stripper at ground level (horizontal lay-out);
- the total condensation of $NH_3$ and $CO_2$ vapours from the stripper in the carbamate condenser allows the separation and removal from the loop (vent) of the main part of inerts (mainly air introduced through the $CO_2$ to protect equipment against corrosion) contained in the vapours effluent from the stripper. In this way the content of inerts in the reactor is minimised with consequently better $CO_2$ conversion efficiency.

SHORT DESCRIPTION OF THE FIGURES

Figure 1:
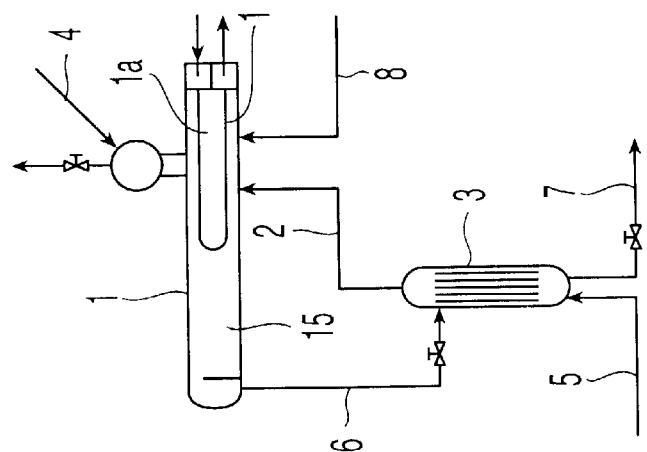

FIG. 1 shows a schematic simplified scheme of the improved Stamicarbon $CO_2$ stripping process loop using an horizontal "pool reactor" 1.

1 represents the horizontal pool reactor being 1a mainly the carbamate condensation zone where an horizontal heat exchanger $1a_1$ is foreseen removing the heat with cooling means and 1b mainly the reaction zone. The horizontal pool reactor 1 is fed through conduit 2 by the vapour streams containing $NH_3$ and $CO_2$ coming from the $CO_2$ stripper 3 and carbamate solution through conduit 4 coming from urea recovery section not represented in FIG. 1. $CO_2$ feed to the loop through conduit 5 is sent to the bottom of the stripper 3 where main portion of carbamate and free ammonia contained in urea solution stream through conduit 6 coming from pool reactor 1 is removed. Urea solution with residual content of carbamate and free ammonia is fed from the bottom of stripper 3 through conduit 7 to the urea recovery unit not represented in FIG. 1. Ammonia feed is sent to "pool reactor" through conduit 8.

FIG. 2 represents a schematic simplified scheme of the improved Toyo $CO_2$ stripping process loop using a vertical pool condenser 1. 1 represents a vertical "pool condenser" where the vapours coming from $CO_2$ stripper 2 are totally condensed with steam generation in the heat exchanger 3 located in the bottom zone 1a of the condenser, and reaction to form urea is started in condenser upper zone 1b. Inerts introduced in the loop through $CO_2$ feed are separated and vented from the condenser top zone through conduit 4. The reactor space 5 is fed through conduit 6 with part of $CO_2$ feed and through conduit 7 with ammonia feed pre-heated in exchanger 8. The ammonia feed being sent to the reactor 5 through an ejector 9 as driving fluid to recycle to the reactor the carbamate solution coming from carbamate condenser 1 fed to the ejector through conduit 10. The carbamate solution recycle with feed ammonia are sent together through ejector 9 and conduit 11 to reactor 5. The reactor effluent is sent through conduit 12 to $CO_2$ stripper 2 where most of the carbamate and free ammonia are removed from the urea solution as vapours and fed through conduit 13 to carbamate condenser 1. Part of the $CO_2$ feed is sent as stripping agent to the bottom of the stripper through conduit 14. From bottom of the stripper the urea solution with a residual content of carbamate and free ammonia, through conduit 15 is sent to the urea recovery unit not represented in FIG. 2.

FIG. 3 shows a schematic simplified scheme of the Snamprogetti "self stripping" process loop where 1 represents the reactor space which is fed through conduit 2 with $CO_2$ feed and conduit 3 with ammonia feed. The ammonia feed being sent to the reactor 1 through an ejector 4 as driving fluid to recycle to the reactor the carbamate solution coming from carbamate condenser 5 fed to the ejector through conduit 6. The carbamate solution recycle with feed ammonia are sent together through ejector 4 and conduit 7 to the reactor 1. The reactor effluent is sent through conduit 8 to stripper 9, generally operating in self stripping mode without any stripping agent from the external. In stripper 9 most of the carbamate and free ammonia are removed from the urea solution as vapours and fed through conduit 10 to carbamate condenser 5. The urea solution with a residual content of carbamate and free ammonia through conduit 11 is sent to the urea recovery unit not represented in FIG. 3.

Figure 4:
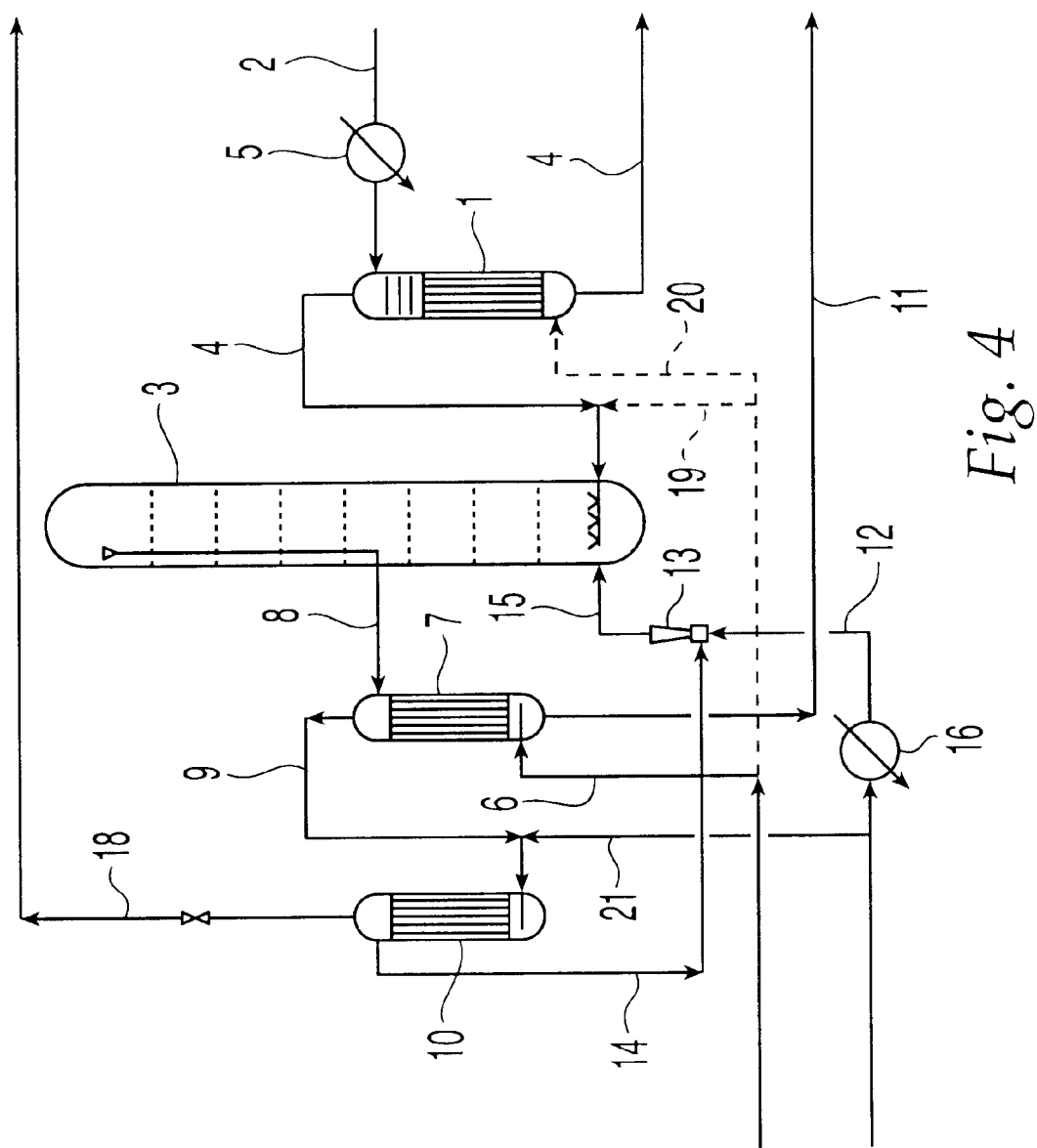

FIG. 4 represents a preferred embodiment of the urea synthesis loop based on $CO_2$ stripping scheme according to the invention. The loop comprises a carbamate stripper 1 where the carbamate water solution coming from the urea recovery unit, not represented in FIG. 4, through conduit 2 is fed to the top of the apparatus. In carbamate stripper 1 main part of carbamate and free ammonia are removed from the water solution as ammonia and $CO_2$ vapours with very low content of water which through conduit 17 are fed to the urea reactor 3. The water solution with a residual content of carbamate and free ammonia is sent back to the urea recovery unit, not represented in FIG. 4, through conduit 4. According to a preferred embodiment carbamate solution from urea recovery unit is pre-heated before reaching the carbamate stripper 1 by heat exchanger 5. Feed $CO_2$ through conduit 6 is sent to $CO_2$ stripper 7 where most of the unreacted carbamate and free ammonia coming from reactor 3 through conduit 8 are removed from urea solution as ammonia and $CO_2$ vapours fed through conduit 9 to the carbamate condenser 10. The urea solution still with residual content of carbamate and free ammonia is fed through conduit 11 to the urea recovery unit not represented in the figure. $NH_3$ feed is pre-heated in exchanger 16 and then partially sent to ejector 13, through conduit 12 while the balance is sent to carbamate condenser 10 through conduit 21. $NH_3$ feed is the driving fluid to recycle the carbamate solution coming from carbamate condenser 10 through conduit 14 to the reactor 3 through conduit 15. Most of the inerts in the $CO_2$ feed, fed to the loop through conduit 6, are removed from carbamate condenser head through conduit 18. According to a preferred embodiment more than 90% $CO_2$ feed is sent to the $CO_2$ stripper 7. The balance is directly sent to reactor 3 through conduit 19. The possibility to use a minor portion of $CO_2$ feed to be sent to the carbamate stripper 1 through conduit 20 is also foreseen.

DETAILED DESCRIPTION OF THE INVENTION

A detailed description of the invention concerning an urea production high efficiency, low investment synthesis loop based on a $CO_2$ stripping scheme, is given with reference to FIG. 4, which represent a preferred embodiment of the invention.

The synthesis loop process and apparatus consist of:
performing a reaction between ammonia ($NH_3$) and carbon dioxide ($CO_2$) in a vertical reaction space 3 (Reactor) operating at 180÷210° C. to obtain a mixture comprising urea with minimum residual content of unreacted $CO_2$ (maximum $CO_2$ intrinsic conversion yield) in presence of minimum content of water ($H_2O/CO_2$ mole ratio at reactor inlet lower than 0.3 preferably 0.1–0.2) and of High Efficiency Trays (HET);
subjecting said reaction mixture to a stripping treatment with the use of $CO_2$ feed as stripping agent in a counter current apparatus 7 (Stripper) operating at 160–210° C. to remove most of the unreacted $CO_2$ and $NH_3$ and to obtain a first flow comprising $NH_3$ and $CO_2$ in vapour phase sent to the carbamate condenser 10 and a second flow comprising urea and residual carbamate and free $NH_3$ in aqueous solution, such residual carbamate and free $NH_3$ being removed downstream the loop in a urea recovery unit, and recycled to the loop in a third flow aqueous solution (carbamate recycle solution: CRS) according to means which are not the subject matter of the present invention (urea recovery unit: URU) to separate the urea product in aqueous solution;
subjecting said first flow comprising $NH_3$ and $CO_2$ in vapour phase to total condensation in a carbamate condenser 10 (Carbamate Condenser) operating at 150–210° C. to obtain a carbamate solution which is sent to the bottom zone of the reactor 3 using an ejector 13;

in a preferred embodiment above carbamate condenser is a vertical heat exchanger designed to work "full of liquid";

in a preferred embodiment the carbamate condensation is obtained removing the heat through steam generation (steam pressure 3–10 kg/cm² g);

separation and removal from carbamate condenser top head of main part of inerts (mainly air introduced through the $CO_2$ to protect equipment against corrosion) contained in the vapours effluent from the stripper;

subjecting at least part of said third flow (carbamate recycle solution CRS) to a treatment in a vertical counter current exchanger 1 (Carbamate Stripper) working at 160–210° C. for carbamate decomposition and removal of free ammonia to obtain a vapour flow containing $CO_2$ and $NH_3$ with minimum content of water, and a weak water carbamate solution sent back to the urea recovery unit URU;

in a preferred embodiment the above Carbamate Stripper is a vertical heat exchanger working in countercurrent mode with trays in the top head;

in a preferred embodiment the above carbamate recycle solution is pre-heated in exchanger 5 up to 100–150° C., preferably with the steam generated in the Carbamate Condenser, before being sent to Carbamate Stripper;

feeding the vapour flow containing $CO_2$ and $NH_3$ with minimum content of water directly to the bottom zone of the reactor 3;

in a preferred embodiment the reactor 3 is equipped with High Efficiency Trays (HET);

feeding most of the $NH_3$ feed through ejector 13 to said reactor bottom together with carbamate solution stream from carbamate condenser 10 and the balance to the carbamate condenser;

in a preferred embodiment the $NH_3$ feed sent to the reactor is pre-heated up to 100–150° C. in exchanger 16 preferably with the steam generated in the carbamate condenser, before being sent to the reactor;

feeding reactor effluent from top of upper part of reactor to stripping treatment with the use of most, preferably more than 90% and the case being all of $CO_2$ feed;

the possibility to use a minor portion of $CO_2$ feed directly sent to the carbamate stripper 1 is also foreseen.

Most of the inerts in the $CO_2$ feed (air or oxygen is generally added to the $CO_2$ feed as passivating agent against corrosion of apparatus) are removed from carbamate condenser head and not sent to the reactor 3, minimising the content of inerts in the reactor with consequent better $CO_2$ feed efficiency. The reactor operates in fact at lower temperatures and has lower surfaces to be passivated, requiring just a fraction of the oxygen introduced in the loop.

It has been found, surprisingly, a synergic effect of the use of High Efficiency Trays (HET) to achieve higher $CO_2$ conversion when in presence of low $H_2/CO_2$ molar ratios, preferably with ratio lower than 0.3.

It has been found that in the carbamate stripper particularly satisfactory results in terms of maintenance and useful capacity can be obtained by the presence of trays in the top head of the exchanger as foreseen in the invention.

Advantageously, according to the invention, all above-mentioned loop components operate practically isobarically at a pressure of 140–180 kg/cm² g.

The advantageous features of the invention are:

the vapour flow containing $CO_2$ and $NH_3$ with minimum content of water fed at least in part directly to the reactor, secure the heat balance of the same without the need to use part of the $CO_2$ feed to be sent to the reactor to sustain the reactor heat balance;

almost all and even all $CO_2$ feed can be used in the stripper for an efficient $CO_2$ stripping of urea solution effluent from reactor.

Further advantages are:

maximum $CO_2$ intrinsic conversion yield in presence of minimum content of water ($H_2O$) and the High Efficiency Trays in the reactor with consequent maximum stripping efficiency;

the total condensation in the carbamate condenser (preferably of "full of liquid" vertical shape) to obtain a carbamate solution of the vapours comprising $NH_3$ and $CO_2$ coming from the $CO_2$ stripper, significantly increase the carbamate solution residence time in the condenser with formation of urea which contribute to increase the total reaction zone residence time;

the total condensation of $NH_3$ and $CO_2$ vapours in the carbamate condenser allows the recycle of carbamate solution with the use of ejector driven by at least part of $NH_3$ feed, with all loop main components: carbamate condenser, stripper, reactor and carbamate stripper at ground level (horizontal lay-out);

the total condensation of $NH_3$ and $CO_2$ vapours from the stripper in the carbamate condenser allows the separation of the main part of inerts (mainly air introduced through the $CO_2$ to protect equipment against corrosion) contained in the vapours effluent from the stripper and minimise the content of inerts in the reactor with consequent better $CO_2$ conversion efficiency;

the pre-heating of carbamate solution before stripping in a carbamate stripper equipped with trays in the top head with steam and of the ammonia feed sent to the reactor with steam produced in carbamate condenser reduces energy consumption.

What is claimed is:

1. Process for urea production in a synthesis loop based on $CO_2$ stripping which comprises the following steps of:

performing a reaction between ammonia ($NH_3$) and carbon dioxide ($CO_2$) in a vertical reaction space (reactor R) to obtain a mixture comprising urea with minimum residual content of unreacted $CO_2$ (maximum $CO_2$ intrinsic conversion yield) in presence of minimum content of water ($H_2O$);

subjecting said reaction mixture to a stripping treatment with the use of $CO_2$ feed as stripping agent in a counter current apparatus (Stripper) to remove most of the unreacted $CO_2$ and $NH_3$ and to obtain a first flow comprising $NH_3$ and $CO_2$ in vapour phase and a second flow comprising urea and residual carbamate and free $NH_3$ in aqueous solution, such residual carbamate and free $NH_3$ being removed downstream the loop in a urea recovery unit, and recycled to the loop in a third flow aqueous solution (carbamate recycle solution: CRS);

subjecting said first flow comprising $NH_3$ and $CO_2$ in vapour phase to total condensation in a carbamate condenser to obtain a carbamate solution which is sent to the bottom zone of the reactor space R using an ejector E;

subjecting at least part of said third flow (carbamate recycle solution CRS) to a treatment (carbamate stripper) of carbamate decomposition and removal of free ammonia to obtain a vapour flow containing $CO_2$ and $NH_3$ with minimum content of water, and a weak water carbamate solution sent back to the urea recovery unit URS;

directly feeding at least part of above vapour flow containing $CO_2$ and $NH_3$ with minimum content of water to the bottom zone of the reaction space.

2. Process as per claim 1 according which at least part of the $NH_3$ feed is fed through ejector to said reaction bottom space together with carbamate solution stream from carbamate condenser.

3. Process as per claim 1 according which the said first flow comprising $NH_3$ and $CO_2$ in vapour phase total condensation takes place in a "full of liquid" carbamate condenser.

4. Process as per claim 1 according which the content of water at the inlet of the reaction space is such that the $H_2O/CO_2$ mol ratio in the reactor is lower than 0.4, preferably lower than 0.2.

5. Process as per claim 1 according which the reaction space in the reactor, the stripper, the carbamate condenser and the carbamate stripper are operating substantially at isobaric mode.

6. Process as per claim 1 according which the carbamate condenser is cooled producing steam which is partially used to pre-heat the carbamate solution recycle (CSR) and at least part of $NH_3$ feed to the reactor.

7. Process as per claim 1 according which the main portion of inerts containing $O_2$ for passivation is vented from carbamate condenser and not sent to the reactor.

8. Process as per claim 1 according which reactor is equipped with High Efficiency Trays.

9. Process as per claim 1 according which carbamate stripper is equipped with trays in the top head of apparatus.

10. Process as per claim 1 according which the carbamate solution recycle is pre-heated before being sent to carbamate stripper.

* * * * *